(12) United States Patent
Choi et al.

(10) Patent No.: US 8,889,916 B2
(45) Date of Patent: Nov. 18, 2014

(54) CATALYST COMPOSITION FOR HYDROFORMYLATION REACTION AND HYDROFORMYLATION PROCESS USING THE SAME

(75) Inventors: Jae-Hui Choi, Daejeon (KR); Dong-Hyun Ko, Daejeon (KR); O-Hak Kwon, Daejeon (KR); Sung-Shik Eom, Daejeon (KR); Moo-Ho Hong, Daejeon (KR); Hye-Won Yang, Seoul (KR)

(73) Assignee: LG Chem, Ltd. (KR)

(*) Notice: Subject to any disclaimer, the term of this patent is extended or adjusted under 35 U.S.C. 154(b) by 30 days.

(21) Appl. No.: 13/192,829

(22) Filed: Jul. 28, 2011

(65) Prior Publication Data
US 2012/0059195 A1 Mar. 8, 2012

(30) Foreign Application Priority Data

Sep. 2, 2010 (KR) ........................ 10-2010-0085890
Apr. 8, 2011 (KR) ........................ 10-2011-0032566

(51) Int. Cl.
*C07C 45/50* (2006.01)
*B01J 31/24* (2006.01)
*B01J 31/22* (2006.01)
*B01J 31/20* (2006.01)

(52) U.S. Cl.
CPC ............ *C07C 45/50* (2013.01); *B01J 2531/845* (2013.01); *B01J 31/2404* (2013.01); *B01J 2531/822* (2013.01); *B01J 2531/827* (2013.01); *B01J 31/2234* (2013.01); *B01J 2231/321* (2013.01); *B01J 31/20* (2013.01)
USPC ............................ 568/454; 502/155; 502/162

(58) Field of Classification Search
USPC .................................. 568/454; 502/155, 162
See application file for complete search history.

(56) References Cited

U.S. PATENT DOCUMENTS

2008/0281128 A1 11/2008 Karvinen et al.

FOREIGN PATENT DOCUMENTS

| CN | 101801528 A | 8/2010 |
|---|---|---|
| EP | 2404671 A2 | 1/2012 |
| KR | 20070116109 A | 12/2007 |
| KR | 20090028251 A | 3/2009 |
| KR | 20100092169 A | 8/2010 |
| KR | 20100092399 A | 8/2010 |
| WO | 0220448 A1 | 3/2002 |
| WO | 2009/035204 A1 | 3/2009 |
| WO | 2010/093208 A2 | 8/2010 |

OTHER PUBLICATIONS

Wood et al. Formate Formation during Co2 (Co)8/ PR3-Catalyzed Hydroformylation. Organometallics, 1984, vol. 3, 170-174.*
International Search Report & Written Opinion PCT/KR2011/005173, dated Mar. 28, 2012.
Oxo Chemicals, "SRI Report", Chemical Economics Handbook, p. 7 (2006).
Robert et al., Organometallics 1986, vol. 5, pp. 466-473.
China Office Action dated Jun. 5, 2014.
Supplemental European Search Report dated Jul. 25, 2014.

* cited by examiner

*Primary Examiner* — Sikarl Witherspoon
(74) *Attorney, Agent, or Firm* — Lerner, David, Littenberg, Krumholz & Mentlik, LLP

(57) ABSTRACT

The present invention relates to a catalyst composition for hydroformylation reaction and a hydroformylation process using the same. In the hydroformylation process using the catalyst composition according to the present invention, increased catalytic stability and high catalytic activity can be obtained, and the selectivity of iso-aldehyde produced can be desirably controlled.

17 Claims, No Drawings

CATALYST COMPOSITION FOR HYDROFORMYLATION REACTION AND HYDROFORMYLATION PROCESS USING THE SAME

CROSS-REFERENCE(S) TO RELATED APPLICATIONS

This application claims priority from Korean Patent Application Nos. 10-2010-0085890 and 10-2011-0032566, filed on Sep. 2, 2010 and Apr. 8, 2011, respectively, in the Korean Intellectual Property Office, the disclosures of which are incorporated herein by reference in their entirety.

TECHNICAL FIELD

The present invention relates to a catalyst composition for a hydroformylation reaction and a hydroformylation process using the same, and more particularly, to a catalyst composition that include a transition metal catalyst and a monodentate phosphine ligand for olefin-based compounds, and a hydroformylation process using the same.

BACKGROUND OF THE INVENTION

A hydroformylation reaction producing linear (normal) and branched (iso) aldehyde which has one more carbon atoms than olefin by reacting carbon monoxide (CO) and hydrogen ($H_2$) that are commonly called as a synthesis gas in the presence of a homogeneous organicmetalic catalyst and a ligand was originally discovered by Otto Roelen in Germany in 1938.

In general, the hydroformylation reaction that is known as oxo reaction, is a very important industrial reaction in view of a homogeneous system catalyst reaction. Currently, about 9,600,000 tons of adhehydes (including alcohol derivatives) are produced by the oxo process all over the world (*SRI report*, September 2006, 682. 7000 page 7).

Various types of aldehydes produced by the oxo reaction are oxidated to carboxylic acids or hydrogenated to alcohols. In addition, aldehydes can also be converted to long alkyl chain-containing acids or alcohols through aldol condensation and then oxidation or reduction. In particular, hydrogenation alcohol of aldehyde, which is obtained by the oxo reaction, as is called oxo alcohol. Oxo alcohol is industrially extensively used as a solvent, additive, various types of raw materials of plasticizers, or synthetic lubricants.

It is known that a metal carbonyl compound catalyst has a catalytic activity of the hydroformylation reaction, and almost focused on cobalt (Co) rhodium (Rh). The N/I (ratio of linear (normal) to branched (iso) isomers) selectivity, activity, and stability of aldehydes vary according to the type of ligand used and operating conditions.

To date, a rhodium-based low-pressure oxo process (LPO process) has been adopted in at least 70% of oxo plants worldwide because of the high efficiency, high yield of normal products, and mild reaction condition even though there are disadvantages of the expensive catalyst and catalytic deactivation due to the poisoning.

A central metal of oxo metal may be used a transition metal, such as iridium (Ir), ruthenium (Ru), osmium (Os), platinum (Pt), palladium (Pd), iron (Fe), or nickel (Ir). In respects to the transition metals, it is known that the order of the catalytic activity is Rh>>Co>Ir, Ru>Os>Pt>Pd>Fe>Ni and the like.

Pt and Rh as Group 8 transition metal have been mainly used in an oxo process, for example, $HCo(CO)_4$, $HCo(CO)_3 PBu_3$ and $HRh(CO)(PR_3)_3$. Pt and Ru are mainly subjects of academic interest. Therefore, Co applied for academic research, and currently most of oxo processes having industrial objects basically uses rhodium and cobalt, and a representative example may include $HCo(CO)_4$, $HCo(CO)_3 PBu$, and $HRh(CO)(PR_3)_3$.

Examples of the ligand that is used during the oxo process include phosphine ($PR_3$, R is $C_6H_5$, or n-$C_4H_9$), phosphine oxide ($O=P(C_6H_5)_3$) and phosphite. In case of using rhodium as the central metal, it is known that the ligand having the catalytic activity and the stability that are better than those of triphenylphosphine (TPP) is almost not present. Thus, in most oxo process, rhodium (Rh) metal is used as a catalyst and TPP is used as a ligand. In addition, to increase the stability of a catalytic system, TPP ligand is used in an amount of at least 100 equivalent of the catalyst.

Since the value of linear aldehyde derivative is generally high among aldehydes that are products of the oxo reaction, many studies have been made to increase the ratio of the linear aldehyde in respects to the catalyst. However, recently, products obtained by using iso-aldehyde as the raw materials instead of the linear aldehyde, for example, an isobutyric acid, neopentyl glycol (NPG), 2,2,4-trimethyl-1,3-pentanediol, isovaleric acid and the like have been developed, thus the use of iso-aldehyde has been increased. Accordingly, there is a demand to develop a technology of producing iso-aldehyde required in a market by desirably controlling the N/I selectivity while the excellent catalytic activity and stability, together with reduced amount of ligand.

SUMMARY OF THE INVENTION

The present invention has been made keeping in mind the above problems occurring in the related art, and thus the inventors of the present invention have found that if a monodentate phosphine ligand is applied to a hydroformylation reaction of olefin at the same time, the catalyst activity and stability are excellent, a ligand is used as reduced amount, and an iso-aldehyde selectivity can be controlled.

Therefore, an aspect of the present invention is to provide catalyst compositions containing a transition metal catalyst and a monodentate phosphine ligand, and a hydroformylation process using the same, in which the catalyst compositions can increase a catalytic stability, decrease the amount of ligand, show a high catalytic activity, and also increase a selectivity of iso-aldehyde produced, at the same time.

DETAILED DESCRIPTION

Accordingly, the present invention provides a catalyst composition for a hydroformylation reaction that includes a monodentate phosphine ligand represented by the following Formula 1; and a transition metal catalyst represented by the following Formula 2:

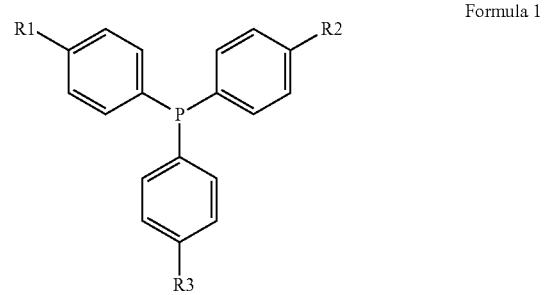

Formula 1 wherein $R_1$, $R_2$ and $R_3$ are each independently an alkyl group having 1 to 3 carbon atoms; or an alkoxy group having 1 to 5 carbon atoms.

$$M(L^1)x(L^2)y(L^3)z \quad \text{Formula 2}$$

wherein M is any one selected from cobalt (Co), rhodium (Rh) and iridium (Ir), $L^1$, $L^2$ and $L^3$ are each independently any one selected from the group consisting of hydrogen, CO, cyclooctadiene, norbornene, chlorine, triphenylphosphine or acetylacetonato, x, y and z are each independently 0 to 5, x, y and z are not 0 at the same time.

In addition, the present invention provides a hydroformylation process of an olefin-based compound, which includes a reacting the olefin-based compound, and a synthesis gas of carbon monoxide and hydrogen in the presence of the catalyst composition according to the present invention to produce aldehydes.

Hereinafter, the present invention will be described in more detail.

The present invention relates to a catalyst composition for hydroformylation reaction containing (a) a monodentate phosphine ligand represented by the following Formula 1; and (b) a transition metal catalyst represented by the following Formula 2:

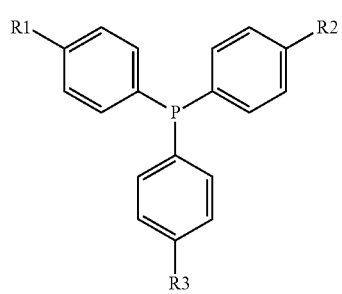

Formula 1 wherein $R_1$, $R_2$ and $R_3$ are each independently an alkyl group having 1 to 3 carbon atoms; or an alkoxy group having 1 to 5 carbon atoms.

The present invention excludes that $R_1$, $R_2$, and $R_3$ are each independently substituted by any one selected from the group consisting of a nitro group (—$NO_2$), a fluorine group (—F), a chlorine group (—Cl), a bromine group (Br), and a silyl group (—SiR, wherein R is selected from hydrogen, alkyl group or alkoxy group); or $R_1$ to $R_3$ are all hydrogen as the monodentate phosphine ligand.

$$M(L^1)x(L^2)y(L^3)z \quad \text{Formula 2}$$

wherein M is any one selected from cobalt (Co), rhodium (Rh) and iridium (Ir), $L^1$, $L^2$ and $L^3$ are each independently any one selected from the group consisting of hydrogen, CO, cyclooctadiene, norbornene, chlorine, triphenylphosphine or acetylacetonato, and x, y and z are each independently 0 to 5, x, y and z are not 0 at the same time.

The catalyst composition for a hydroformylation reaction containing the monodentate phosphine compound represented by the above Formula 1 as ligand according to the present invention has technical features such that increased catalytic stability and high catalytic activity can be obtained, and the selectivity of iso-aldehyde produced can be desirably controlled.

Each of the constituents of the catalyst composition for a hydroformylation reaction will be described in detail.

(a) A Monodentate Phosphine Ligand

It is preferable that the catalyst composition includes a monodentate phosphine ligand represented by the above Formula 1. The monodentate phosphine ligand is continuously consumed during an aldehyde recovering process of a continuous hydroformylation process. Accordingly, a desirable ligand is selected in consideration of the desired iso-aldehyde selectivity and injected into the reactor. Thus, it is easy to apply the above ligands in practice.

According to the catalyst composition of the present invention and the hydroformylation process using the same, the monodentate phosphine ligand alone are applied to the hydroformylation reaction of olefin to obtain increased catalytic stability, high catalytic activity and reduced ligand amounts together with controlling desirably the selectivity of iso-aldehyde produced.

It is preferable that the monodentate phosphine ligand represented by the above Formula 1 be one or more selected from the group consisting of tri-p-tolylphosphine (TPTP), tri-p-ethylphenylphosphine (TPEtPP), tris-p-metoxyphenyl phosphine (TMPP) and tri-p-isopropoxyphenyl phosphine (TIPPP). Preferably, the monodentate phosphine ligand is one or more selected from the group consisting of tri-p-tolylphosphine (TPTP) represented by the following Formula 4, and tris-p-methoxyphenyl phosphine (TMPP) represented by the following Formula 5:

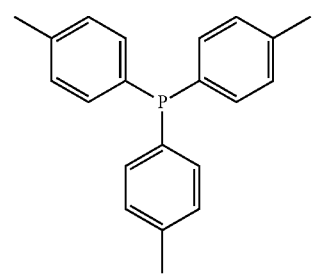

Formula 4

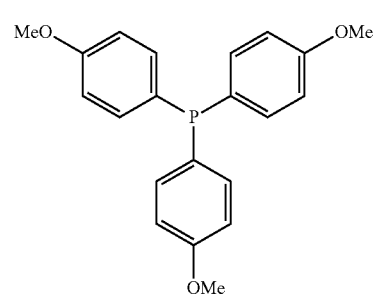

Formula 5

The content of the monodentate phosphine ligand represented by the above Formula 1 is preferably in the range of 5 to 100 mole, and more preferably in the range of 10 to 50 mole, based on 1 mole of central metal of the transition metal catalyst represented by the above Formula 2. In connection with this, if the content is less than 5 mole based on 1 mole of central metal of the transition metal catalyst, there is a problem in poor reactivity of catalyst. If the content is more than 100 mole, there is a problem in reduced reaction velocity due to the excessive amount of the costly ligand.

Preferably, the content of the monodentate phosphine ligand represented by the Formula 1 is in the range of 1.5 to 4.0 wt % based on total weight of the catalyst composition. In connection with this, if the content is less than 1.5 wt % based on total weight of the catalyst composition, there is a problem in the catalytic stability. If the content exceeds 4.0 wt %, since an excessive amount of the costly ligand is used without any additional benefit, there is a problem in that cost is increased.

More preferably, the content is in the range of 1.5 to 3.0 wt % based on total weight of the catalyst composition as the catalytic activity may be maximized and also N/I selectivity can be improved.

Particularly, in case of using tri-p-tolylphosphine (TPTP) represented by the above Formula 4 as the ligand, the content is preferably in the range 2.0 to 3.0 wt % based on total weight of the catalyst composition, and selectivity for iso-aldehyde, and in case of using tris-p-methoxyphenyl phosphine (TMPP) represented by the above Formula 5, the content is preferably in the range of 1.5 to 2.1 wt % based on total weight of the catalyst composition, for providing maximized catalytic stability, catalytic activity.

More preferably, the monodentate phosphine ligand is a mixture of tri-p-tolylphosphine (TPTP) represented by the Formula 4 and tris-p-methoxyphenyl phosphine (TMPP) represented by the Formula 5.

In case of when the monodentate is used as a mixture of tri-p-tolylphosphine (TPTP) represented by the above Formula 4 and tris-p-methoxyphenyl phosphine (TMPP) represented by the above Formula 5, may vary, preferably be in the range of 1 to 2 wt % of TPTP and 0.5 to 1.0 wt % of TMPP based on total weight of the catalyst composition in respects to the catalytic stability and N/I selectivity.

(b) Transition Metal Catalyst

In respects to the transition metal catalyst that is represented by the above Formula 2, there are cases of when $L^1$ is CO, $L^2$ is acetylacetonato, and x, and y are 2 and 1, respectively (z is 0), when $L^1$ is CO, $L^2$ is acetylacetonato, $L^3$ is triphenylphosphine, and x, y and z are all 1, and when $L^1$ is CO, $L^2$ is hydrogen, $L^3$ is triphenylphosphine, x, y and z are each independently 1, 1 and 3.

Preferably, the transition metal catalyst represented by the above Formula 2 be one or more selected from the group consisting of cobaltcarbonyl $[CO_2(CO)_8]$, acetylacetonatodicarbonylrhodium $[Rh(AcAc)(CO)_2]$, acetylacetonatocarbonyltriphenylphosphinerhodium [Rh(AcAc)(CO)(TPP), ROPAC], hydridocarbonyltri(triphenylphosphine)rhodium $[HRh(CO)(TPP)_3]$, acetylacetonatodicarbonyliridium $[Ir(AcAc)(CO)_2]$, and hydridocarbonyltri(triphenylphosphine)iridium $[HIr(CO)(TPP)_3]$.

More preferably, the transition metal catalyst is selected from acetylacetonatodicarbonylrhodium $[Rh(AcAc)(CO)_2]$ and/or acetylacetonatocarbonyltriphenylphosphinerhodium [Rh(AcAc)(CO)(TPP), ROPAC].

In the case of when L in the transition metal catalyst represented by the above Formula 2 is triphenyphosphine, it is substituted by Formula 4 or Formula 5 as ligand having an excellent accessibility to metal electronically after addition to the reactor, so that it does not have any adverse effect for the reaction and the ligands are continuously consumed during an aldehyde recovering process of a continuous hydroformylation process.

Preferably, in respects to the content of the above transition metal catalyst represented by the above Formula 2, the content of the central metal is in the range of 10 to 1000 ppm (parts per million) based on a weight or a volume of the catalyst composition. More preferably, the content is in the range of 50 to 500 ppm. In case of when the content of the transition metal is less than 10 ppm, since the reaction rate of the hydroformylation is slow, it is undesirable in practice. In case of when the content of the transition metal is more than 1000 ppm, since the transition metal is costly, the cost is increased and the excellent effect is not obtained in terms of the reaction rate.

In addition, the present invention relates to a hydroformylation process of an olefin-based compound, which includes a reacting the olefin-based compound, and a synthesis gas of carbon monoxide and hydrogen in the presence of the catalyst composition according to the present invention to produce aldehydes.

The specific components and contents of the catalyst composition are as mentioned above. The catalyst composition may be produced by dissolving the above components in a solvent.

In the above hydroformylation process, examples of the above solvent may include one or more compounds selected from the group consisting of aldehydes including propane aldehyde, butyl aldehyde, phentyl aldehyde, and valer aldehyde; ketones including acetone, methyl ethyl ketone, methyl isobutyl ketone, acetophenone, and cyclohexanone; alcohols including ethanol, pentanol, octanol, and thesanol; aromatic compounds including benzene, toluene, and xylene; halogenated aromatic compounds including ortho-dichlorobenzene; ethers including tetrahydrofurane, dimethoxyethane, and dioxane; halogenated paraffins including methylene chloride; and paraffin hydrocarbons including such as heptane. More preferably, aldehyde produced from the hydroformylation reaction may be used.

In the above hydroformylation process, it is preferable that the above olefin-based compound be a compound that is represented by the following Formula 3:

Formula 3 wherein $R_4$ and $R_5$ are each independently any one selected from the group consisting of hydrogen, an alkyl group having 1 to 20 carbon atoms, a fluorine group (—F), a chlorine group (—Cl), a bromine group (—Br), a trifluoromethyl group (—$CF_3$) and an aryl group having 0 to 5 substituent groups and 6 to 20 carbon atoms, and the substituent group is nitro (—$NO_2$), fluorine (—F), chlorine (—Cl), bromine (—Br), a methyl group, an ethyl group, a propyl group or a butyl group when the aryl group is substituted.

Specifically, the olefin-based compound represented by the Formula 3 may be one or more compounds selected from the group consisting of ethane, propene, 1-butene, 1-pentene, 1-hexene, 1-octene, and styrene.

In the above hydroformylation process, the composition ratio of carbon monoxide to hydrogen ($CO:H_2$) that are the synthesis gas may vary, preferably be in the range of about 5:95 to 70:30, more preferably about 40:60 to 60:40, and most preferably about 50:50 to 40:60. In case of when the mole ratio is less than 5:95 or more than 70:30, since the non-reacted gas in the reaction is too much in the reactor, there is a risk that the reactivity of the catalyst may be decreased.

In the hydroformylation process, other reaction conditions except the catalyst composition may include those known in the art.

For example, in the above hydroformylation process, the hydroformylation process is performed at the reaction temperature in the range of preferably about 20 to 180° C., more preferably about 50 to 150° C., and most preferably about 75 to 125° C. In case of when the reaction temperature is less than 20° C., there is a problem that the hydroformylation reaction is not proceeded. In case of when the reaction temperature is more than 180° C., there is a problem in decreased catalytic activity due to greatly damaged catalytic stability.

In the above hydroformylation process, the hydroformylation process performed at the reaction pressure in the range of preferably about 1 to 700 bar, more preferably about 1 to 300 bar and most preferably about 5 to 30 bar. In case of when the reaction pressure is less than 1 bar, since the hydroformylation reaction is not proceeded, it is undesirable in practice. In case of when the reaction pressure is more than 700 bar, since costly reactor should be used due to the explosion risk of the process without a specific activity advantage, it is undesirable in industrial practice.

The reaction caused by the above hydroformylation process may be shown in the following Reaction Equation 1:

Reaction Equation 1

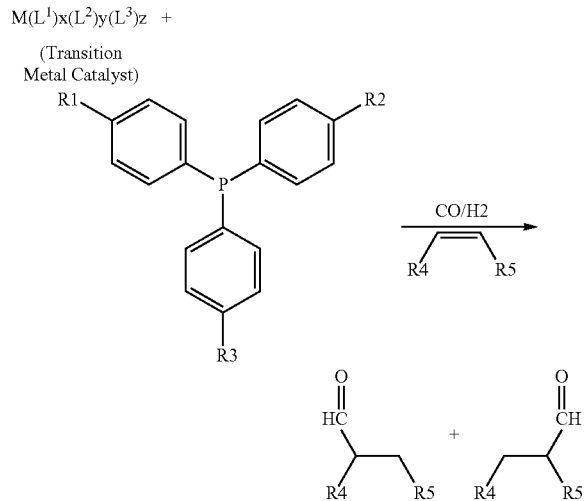

As shown in the Reaction Equation 1, first, the transition metal catalyst and the ligands are dissolved in a solvent such as benzene, toluene, ethanol, pentanol, octanol, hexanol, butylaldehyde, and phentyladehyde to prepare a solution mixture of the catalyst and the ligands.

Then, the olefin-based compound 3, and the synthesis gas 4 of carbon monoxide and hydrogen are injected in conjunction with the solution mixture of the catalyst and the ligands into the reactor, agitated, heated and pressurized to perform the hydroformylation reaction.

According to the catalyst composition of the present invention and the hydroformylation process using the same, the monodentate phosphine ligand are applied to the hydroformylation reaction of olefin to obtain increased catalytic stability, high catalytic activity and reduced ligand amounts together with controlling desirably the selectivity of iso-aldehyde produced.

In addition, the monodentate phosphine ligand is continuously consumed during an aldehyde recovering process of a continuous hydroformylation process. Accordingly, a desirable ligand is selected in consideration of the desired iso-aldehyde selectivity and injected into the reactor. Thus, it is easy to apply the above ligands in practice.

Hereinafter, the present invention will be described in more detail in light of Examples and Comparative Examples.

The present invention may, however, be embodied in many different forms and should not be construed as being limited to the Examples set forth herein. Rather, these Examples are provided such that this disclosure will be thorough and complete and will fully convey the concept of the present invention to those skilled in the art.

Examples 1 to 9

The Hydroformylation Reaction of propene using the acetylacetonatocarbonyltriphenylphosphinerhodium (Rh(AcAc)(CO)(TPP), ROPAC) catalyst, and the monodentate phosphine compound 0.0957 g (0.194 mmol) of ROPAC that was the catalyst, tri-para-tolylphosphine (TPTP), tri-para-ethylphenylphosphine (TPEtPP), tris-para-methoxyphenyl phosphine (TMPP) or tri-para-isoprophoxyphenyl phosphine (TIPPP) that were the monodentate phosphine compound were dissolved in butylaldehyde solvent according to the contents described in Table 1 so that the total weight of the solution was 100 g, and then added in the autoclave reactor having the volume of 600 ml volume. Propene (olefin):CO:$H_2$ were injected into the above reaction solution, and the reaction was performed for 1 hour while the pressure in the reactor was maintained at 8 bar and agitation was performed at 90° C.

The type of the catalyst and the ligand to the above reaction, a weight ratio of the ligand in the catalyst composition, the N/I selectivity, and the catalytic activity are described in Table 1 in the detail.

Examples 10 and 11

Additionally, 0.0501 g (0.198 mmol) of Rh(AcAc)(CO)$_2$ that was the catalyst, tri-para-tolylphosphine (TPTP), tri-para-ethylphenylphosphine (TPEtPP), tris-para-methoxyphenyl phosphine (TMPP) or tri-para-isoprophoxyphenyl phosphine (TIPPP) that were the monodentate phosphine compound were dissolved in butylaldehyde solvent according to the contents described in Table 1 so that the total weight of the solution was 100 g, and then added in the autoclave reactor having the volume of 600 ml.

Propene(olefin):CO:$H_2$ were injected into the above reaction solution, and the reaction was performed for 1 hour while the pressure in the reactor was maintained at 8 bar and the agitation was performed at 90° C.

The types of the catalyst and the ligand to the above reaction, the weight ratio of the ligand in the catalyst composition, the N/I selectivity, and the catalytic activity are described in Table 1 in the detail.

Measurement of Physical Property

N/I selectivity: it is the value divided the amount of normal-butylaldehyde produced from the reaction by the amount of iso-butylaldehyde. The amounts of each aldehyde are obtained by gas-chromatography (GC) analysis.

catalytic activity: it is the value divided total amount of aldehyde produced during the reaction by a molecular weight of butyl aldehyde, a concentration of the used catalyst, and the reaction time. The unit of catalytic activity is mol(BAL)/mol(Rh)/h.

Aging Test: the synthesis gas (CO:$H_2$) having mole ratio of 1:1 was injected into the reaction solution, the reaction was maintained at 10 bar and the agitation was performed at 120° C. and any change during the reaction was evaluated.

Comparative Examples 1 to 8

The Hydroformylation Reaction of Propene by Using acetylacetonatocarbonyltriphenylphosphinerhodium (Rh(AcAc)(CO)(TPP), ROPAC) catalyst, triphenylphosphine compound, tri-p-tolylphosphine (TPTP), tris-p-methoxylphenylphosphine (TMPP), tri(p-chlorophenyl)phosphine (TCPP), tri-o-tolylphosphine (TOTP)

TPP, TPP and TPTP, TPP and TMPP, TCPP, TOTP that were the triphenylphosphine compound were used as the ligand to perform the catalyst activity test by using the same methods as Examples 1 to 11 according to the content described in the following Table, and the results are also described in the following Table 1.

TABLE 1

| No. | Ligand (wt %) | Fresh catalytic activity (kgmol (BAL)/ mol (Rh)/h) | N/I Selectivity | Aging time Fresh | 2.5 hr | 5.0 hr |
|---|---|---|---|---|---|---|
| Com. Ex. 1 | TPP (6) | 0.403 | 9.5 | 0.403 | 0.209 | 0.193 |
| Com. Ex. 2 | TPP (3) | 0.572 | 8.3 | 0.572 | 0.209 | 0.177 |
| Ex. 1 | TPTP (4) | 0.407 | 5.1 | 0.407 | 0.275 | 0.243 |
| Ex. 2 | TPTP (3) | 0.484 | 4.2 | 0.484 | 0.306 | 0.266 |
| Ex. 3 | TPTP (2) | 0.606 | 3.5 | 0.606 | 0.322 | 0.282 |
| Ex. 4 | TPEtPP (2) | 0.530 | 3.3 | 0.530 | 0.318 | 0.280 |
| Ex. 5 | TMPP (2.1) | 0.435 | 3.0 | 0.435 | 0.236 | 0.233 |
| Ex. 6 | TMPP (1.8) | 0.463 | 2.7 | 0.463 | 0.241 | 0.238 |
| Ex. 7 | TMPP (1.5) | 0.504 | 2.5 | 0.504 | 0.302 | 0.262 |
| Ex. 8 | TIPPP (1.5) | 0.423 | 2.4 | 0.423 | 0.244 | 0.242 |
| Ex. 9 | TPTP (1.5) + TMPP (0.8) | 0.488 | 3.3 | 0.488 | 0.303 | 0.254 |
| Ex. 10 | TPTP (2.5) | 0.541 | 3.6 | 0.541 | 0.342 | 0.290 |
| Ex. 11 | TMPP (1.8) | 0.457 | 2.6 | 0.457 | 0.249 | 0.241 |
| Com. Ex. 3 | TPP (3) + TPTP (1.5) | 0.398 | 7.6 | 0.398 | 0.208 | 0.190 |
| Com. Ex. 4 | TPP (3) + TMPP (0.9) | 0.428 | 7.3 | 0.428 | 0.197 | 0.188 |
| Com. Ex. 5 | TPTP (0.5) | 1.562 | 3.3 | 1.562 | 0.476 | 0.203 |
| Com. Ex. 6 | TPTP (6) | 0.274 | 6.8 | 0.274 | 0.180 | 0.164 |
| Com. Ex. 7 | TCPP (6) | 0.525 | 12.9 | 0.525 | 0.225 | 0.159 |
| Com. Ex. 8 | TOTP (6) | 0.826 | 1.4 | 0.826 | 0.001 | 0.000 |

With reference to the above Examples 1 to 11 and Comparative Examples 1 to 8, the catalytic activity is excellent as compared to the case of when only triphenylphosphine ligand is used as the ligand under the same condition, and the case of when triphenylphosphine ligand and monodentate phosphine ligand are used at the same time.

In addition, it can be seen that the N/I selectivity can be improved, and the composition can be used during an oxo process in practice because the stability of the composition is almost similar to that of triphenylphosphine of 120 equivalents based on Rh (Comparative Example 1).

Meanwhile, in the case of when the content of the monodentate phosphine ligand is in the range of 1.5 to 4 wt % based on total weight of the catalyst composition, and more preferably 1.5 to 3 wt %, it is preferable to provide maximized catalytic activity together with improved N/I selectivity. Also it can be seen that in case of no substituents and carbon atoms of 1 to 3 as a para site therein was shown desirable results.

The invention claimed is:

1. A catalyst composition for hydroformylation reaction comprising of:
   (a) one or more phosphine ligands, wherein the one or more phosphine ligands consist of one or more monodentate phosphine ligands represented by the following Formula 1; and
   (b) one or more transition metal catalysts:

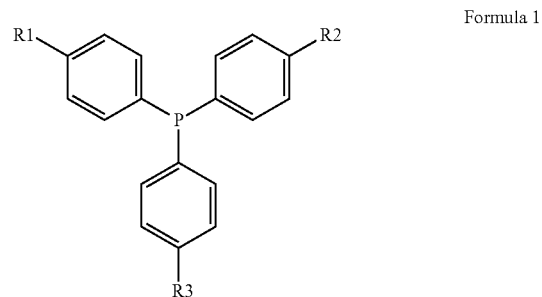

Formula 1 wherein $R_1$, $R_2$ and $R_3$ are each independently an alkyl group having 1 to 3 carbon atoms or an alkoxy group having 1 to 5 carbon atoms,
wherein an amount of the one or more phosphine ligands is in the range of 0.8 to 2.3 wt % based on total weight of the catalyst composition, and
wherein the catalyst composition selectively produces an amount of a normal aldehyde relative to an amount of an iso-aldehyde in a ratio ranging from 2.4 to 3.5.

2. The catalyst composition as set forth in claim 1, wherein the one or more transition metal catalysts (b) is represented by the following Formula 2:

$$M(L^1)x(L^2)y(L^3)z \quad \text{Formula 2}$$

wherein M is any one selected from the group consisting of cobalt (Co), rhodium (Rh) and iridium (Ir), $L^1$, $L^2$ and $L^3$ are each independently any one selected from the group consisting of hydrogen, CO, cyclooctadiene, norbornene, chlorine, triphenylphosphine and acetylacetonato, and
x, y and z are each independently 0 to 5, and x, y and z are not 0 at the same time.

3. The catalyst composition as set forth in claim 1, wherein the one or more monodentate phosphine ligands is one or more selected from the group consisting of tri-p-tolylphosphine (TPTP), tri-p-ethylphenylphosphine (TPEtPP), tris-p-metoxyphenyl phosphine (TMPP) and tri-p-isopropoxyphenyl phosphine (TIPPP).

4. The catalyst composition as set forth in claim 1, wherein the one or more monodentate phosphine ligands is one or more selected from the group consisting of tri-p-tolylphosphine (TPTP) represented by the following Formula 4, and tris-p-methoxyphenyl phosphine (TMPP) represented by the following Formula 5:

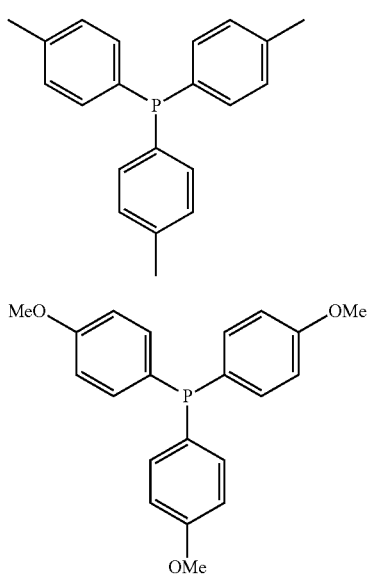

Formula 4

Formula 5

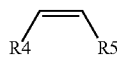

Formula 3 wherein $R_4$ and $R_5$ are each independently any one selected from the group consisting of hydrogen, an alkyl group having 1 to 20 carbon atoms, a fluorine group (—F), a chlorine group (—Cl), a bromine group (—Br), a trifluoromethyl group (—$CF_3$) and an aryl group having 0 to 5 substituent groups and 6 to 20 carbon atoms, wherein the substituent group is nitro (—$NO_2$), fluorine (—F), chlorine (—Cl), bromine (—Br), a methyl group, an ethyl group, a propyl group or a butyl group.

13. The hydroformylation process as set forth in claim 11, wherein the olefin-based compound is one or more compounds selected from the group consisting of ethane, propene, 1-butene, 1-pentene, 1-hexene, 1-octene and styrene.

14. The hydroformylation process as set forth in claim 11, wherein molar ratio of carbon monoxide to hydrogen (CO:$H_2$) of the synthesis gas is in the range of 5:95 to 70:30.

15. The hydroformylation process as set forth in claim 11, wherein the step of reacting is performed at a pressure in the range of 1 to 700 bar.

5. The catalyst composition as set forth in claim 1, wherein a content of the one or more monodentate phosphine ligands is in the range of 5 to 100 mole based on 1 mole of central metal of the transition metal catalyst.

6. The catalyst composition as set forth in claim 4, wherein the one or more monodentate phosphine ligands is tri-p-tolylphosphine (TPTP) represented by the Formula 4, and an amount of the tri-p-tolylphosphine (TPTP) present is 2.0 wt % based on total weight of the catalyst composition.

7. The catalyst composition as set forth in claim 4, wherein the one or more monodentate phosphine ligands is tris-p-methoxyphenyl phosphine (TMPP) represented by the Formula 5, and an amount of the tris-p-methoxyphenyl phosphine (TMPP) present is in the range of 1.5 to 2.1 wt % based on total weight of the catalyst composition.

8. The catalyst composition as set forth in claim 4, wherein the one or more monodentate phosphine ligands is a mixture of tri-p-tolylphosphine (TPTP) represented by the Formula 4 and tris-p-methoxyphenyl phosphine (TMPP) represented by the Formula 5, and an amount of the tri-p-tolylphosphine (TPTP) present is in the range of 1 to 2 wt % and an amount of the tris-p-methoxyphenyl phosphine (TMPP) present is 0.5 to 1.0 wt % based on total weight of the catalyst composition.

9. The catalyst composition as set forth in claim 2, wherein the one or more transition metal catalysts is one or more selected from the group consisting of acetylacetonatodicarbonylrhodium (Rh(AcAc)(CO)$_2$), acetylacetonatocarbonyltriphenylphosphinerhodium (Rh(AcAc)(CO)(TPP)), and hydridocarbonyltri(triphenylphosphine)rhodium (HRh(CO)(TPP)$_3$).

10. The catalyst composition as set forth in claim 2, wherein a content of central metal of the one or more transition metal catalysts is in the range of 10 to 1000 ppm based on weight or volume of the catalyst composition.

11. A hydroformylation process of an olefin-based compound comprising reacting the olefin-based compound at a temperature in the range of 20 to 180° C., a synthesis gas of carbon monoxide and hydrogen in the presence of the catalyst composition according to claim 1 to produce aldehydes.

12. The hydroformylation process as set forth in claim 11, wherein the olefin-based compound is a compound represented by the following Formula 3:

16. The hydroformylation process as set forth in claim 11, wherein the catalyst composition is dissolved in one or more solvent selected from the group consisting of propane aldehyde, butyl aldehyde, phentyl aldehyde, valer aldehyde, acetone, methyl ethyl ketone, methyl isobutyl ketone, acetophenone, cyclohexanone, ethanol, pentanol, octanol, thesanol, benzene, toluene, xylene, ortho-dichlorobenzene, tetrahydrofurane, dimethoxyethane, dioxane, methylene chloride, and heptane.

17. A catalyst composition for hydroformylation reaction consisting of:
(a) one or more monodentate phosphine ligands represented by the following Formula 1;
(b) a transition metal catalyst; and
(c) one or more solvents:

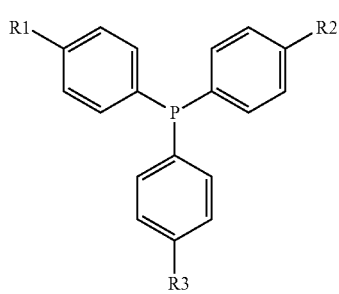

Formula 1 wherein $R_1$, $R_2$ and $R_3$ are each independently an alkyl group having 1 to 3 carbon atoms or an alkoxy group having 1 to 5 carbon atoms,
wherein an amount of the one or more monodentate phosphine ligands is in the range of 0.8 to 2.3 wt % based on total weight of the catalyst composition, and
wherein the catalyst composition selectively produces an amount of a normal aldehyde relative to an amount of an iso-aldehyde in a ratio ranging from 2.4 to 3.5.

* * * * *